(12) United States Patent
Lazeroms et al.

(10) Patent No.: US 7,908,015 B2
(45) Date of Patent: Mar. 15, 2011

(54) SUBCUTANEOUSLY IMPLANTABLE LEAD INCLUDING DISTAL FIXATION MECHANISM

(75) Inventors: Markus J. C. Lazeroms, Vroenhoven-Riemst (BE); Jean J. G. Rutten, Bocholtz (NL); Karel F. A. A. Smits, Munstergeleen (NL)

(73) Assignee: Medtronic, Inc., Minneapolis, MN (US)

( * ) Notice: Subject to any disclaimer, the term of this patent is extended or adjusted under 35 U.S.C. 154(b) by 291 days.

(21) Appl. No.: 12/183,598

(22) Filed: Jul. 31, 2008

(65) Prior Publication Data
US 2010/0030311 A1 Feb. 4, 2010

(51) Int. Cl.
*A61N 1/00* (2006.01)
(52) U.S. Cl. ........................................ 607/116
(58) Field of Classification Search ................ 600/517; 607/116, 3, 5
See application file for complete search history.

(56) References Cited

U.S. PATENT DOCUMENTS

| | | | |
|---|---|---|---|
| 4,913,164 A | 4/1990 | Greene et al. | |
| 4,953,551 A | 9/1990 | Mehra et al. | |
| 5,044,374 A | 9/1991 | Lindemans et al. | |
| 6,093,172 A | 7/2000 | Funderburk et al. | |
| 7,069,075 B2 | 6/2006 | Olson | |
| 7,092,765 B2 | 8/2006 | Geske et al. | |
| 7,236,828 B2 | 6/2007 | Casavant et al. | |
| 7,286,884 B2 | 10/2007 | Marshall et al. | |
| 7,383,085 B2 | 6/2008 | Olson | |
| 2002/0107545 A1 | 8/2002 | Rissman et al. | |
| 2002/0151948 A1 | 10/2002 | King et al. | |
| 2004/0230229 A1 | 11/2004 | Lovett et al. | |
| 2006/0004421 A1 | 1/2006 | Bennett et al. | |
| 2006/0004429 A1* | 1/2006 | Mrva et al. | 607/116 |
| 2007/0203556 A1 | 8/2007 | Rutten et al. | |
| 2007/0255368 A1* | 11/2007 | Bonde et al. | 607/116 |
| 2010/0137930 A1* | 6/2010 | Bardy et al. | 607/5 |

FOREIGN PATENT DOCUMENTS

WO 20080106338 A 9/2008

OTHER PUBLICATIONS

Office Action from U.S. Appl. No. 12/183,568 dated Nov. 16, 2010, 6 pp.

* cited by examiner

*Primary Examiner* — George Manuel
*Assistant Examiner* — Robert N Wieland
(74) *Attorney, Agent, or Firm* — Michael C. Soldner

(57) ABSTRACT

A subcutaneously implantable lead includes a coil disposed along a portion of the lead, and a lead tip coupled to a distal end of the lead. The lead tip includes at least one component that is movable relative to the distal end of the lead and configured to anchor the lead tip in subcutaneous tissue.

19 Claims, 8 Drawing Sheets

SUBCUTANEOUSLY IMPLANTABLE LEAD INCLUDING DISTAL FIXATION MECHANISM

FIELD OF THE INVENTION

The present invention relates generally to subcutaneously implantable leads, and more particularly, to a lead tip having an active distal fixation mechanism employable to subcutaneously secure an implanted lead.

BACKGROUND OF THE INVENTION

Many types of implantable medical devices have been clinically implanted into patient's bodies over the last twenty years that deliver relatively high-energy cardioversion and/or defibrillation shocks to a patient's heart when a malignant tachyarrhythmia, e.g., atrial or ventricular fibrillation, is detected. Cardioversion shocks are delivered in synchrony with a detected R-wave when fibrillation detection criteria are met, whereas defibrillation shocks are delivered when fibrillation criteria are met and an R-wave cannot be discerned from the electrocardiogram. The earliest clinically released automatic implantable defibrillators (AIDs) that were implanted in human patients provided a high energy defibrillation shock developed by an AID implantable pulse generator (IPG) through a pair of epicardial electrodes applied directly to the epicardium of the heart exposed through a thoracotomy when high heart rate detection criteria were met. Later developed and clinically implanted implantable cardiodefibrillators (ICDs), originally referred to as pacemaker/cardioverter/defibrillators (PCDs), possessed more sophisticated detection algorithms and provided defibrillation, R-wave synchronized cardioversion, and pacing therapies to treat a variety of malignant tachyarrhythmias ranging from fibrillation to fast tachycardias. Current ICDs typically additionally possess single or dual chamber bradycardia pacing capabilities for treating specified chronic or episodic atrial and/or ventricular bradycardia and tachycardia. The most current clinically released ICDs also include right and left heart chamber pacing capabilities for improving the cardiac output of patient's hearts that are in heart failure. Unless otherwise indicated, all of the above-described implantable devices are referred to herein as ICDs.

It was postulated early in the development of ICDs that cardioversion/defibrillation shocks could be delivered between large surface area patch electrodes implanted subcutaneously over the rib cage on either side of the heart as indicated in the article by Schuder et al. entitled "Experimental Ventricular Defibrillation with an Automatic and Completely Implanted System", Transactions American Society for Artificial Internal Organs, 16:207, 1970.

Subcutaneous leads are implanted between the patient's skin and rib cage with a tunneling tool. Conventional subcutaneous implantable leads are implanted by first forming a subcutaneous channel with a tunneling tool that is coaxial with a sheath. After the channel is formed, the tool is removed leaving the sheath disposed in the channel. The lead is subsequently threaded down the sheath into a desired subcutaneous position. The sheath is thereafter removed by withdrawing and slitting the sheath to bring the sheath over a proximal end of the lead. Withdrawing the sheath from the channel can undesirably snag the lead and move it from is desired subcutaneous position.

It is desirable to provide implantable leads for use with ICDs that are simpler to place subcutaneously.

DETAILED DESCRIPTION OF THE INVENTION

According to an embodiment of the present invention, a subcutaneously implantable lead is provided that includes a coil disposed along a portion of the lead, and a lead tip coupled to a distal end of the lead. The lead tip includes at least one component that is movable relative to the distal end of the lead and configured to anchor the lead tip in subcutaneous tissue.

According to an embodiment of the present invention, a method of implanting a lead in a patient, where the lead is attachable to an implantable cardiodefibrillator (ICD), includes subcutaneously advancing a lead tip attached to a distal end of the lead through a surgical incision formed in the patient's skin with a tunneling tool that is removably attached to the lead tip; and activating a movable portion of the lead tip from a proximal end of the lead to fix the distal end of the lead in subcutaneous tissue.

In this specification, "anchor" means to fix a position of an object relative to tissue to minimize movement of the object relative to the tissue. Thus, although there may be small movements of the object relative to the tissue, arising for example from body movements of the patient that give rise to small deflections of the object within the tissue, the object is nevertheless "anchored" subcutaneously in the tissue.

It is to be understood that features of the various exemplary embodiments described herein may be combined with each other, unless specifically noted otherwise.

Figure 1:
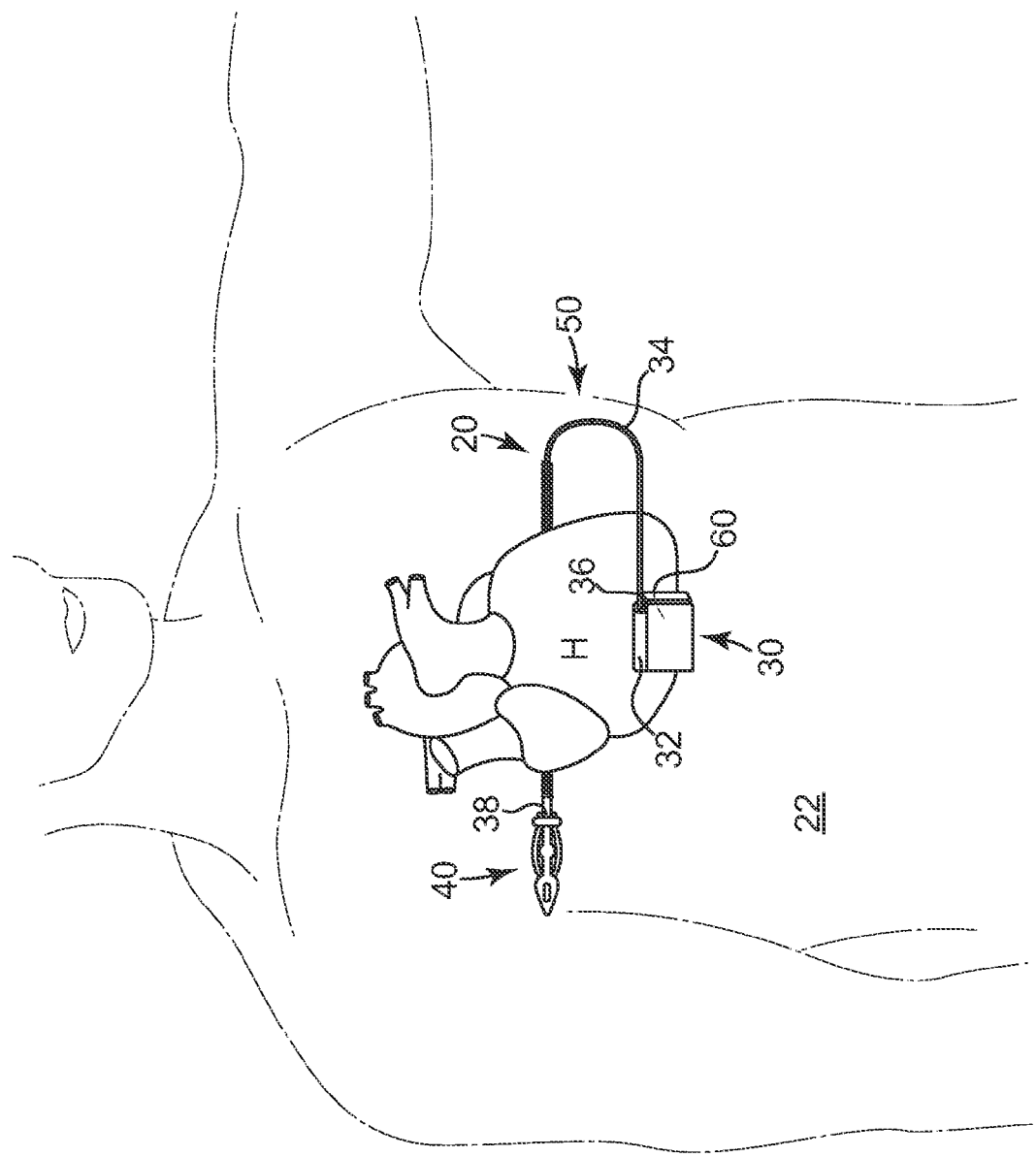
FIG. 1 is a schematic perspective view of an implanted implantable cardiodefibrillator (ICD) including a lead attached to a lead tip according to one embodiment.

FIG. 1 is a schematic illustration of an implantable cardiodefibrillator (ICD) 20 subcutaneously implanted in a patient 22 according to one embodiment. ICD 20 includes a housing 30 including a header 32, a lead 34 including a proximal end 36 coupled to header 32 and a distal end 38 coupled to a lead tip 40. In one embodiment, lead tip 40 is tunneled subcutaneously through an incision 50 to place lead 34 between the patient's 22 skin and rib cage in the region of the heart H. Thereafter, proximal end 36 of lead 34 is connected to header 32 and housing 30 is subcutaneously implanted pectorally within patient 22 between the skin and rib cage.

ICD 20 is implanted subcutaneously outside the thorax and inside the skin. Suitable implantation sites include a posterior region of the patient's rib cage, a paraspinal region of the patient, a parascapular region of the patient, or approximately posterior to a midaxillary line of the patient. In one embodiment, ICD 20 provides subcutaneous defibrillation and pacing without implanted venous epicardial leads. In one embodiment, ICD 20 provides subcutaneous defibrillation and pacing in addition to one or more implanted venous epicardial leads that connect to circuitry within housing 30.

In one embodiment, housing 30 is hermetically sealed to enclose electronic sensing, pacing, and cardioversion/defibrillation circuitry, including high voltage capacitors that are charged and discharged to deliver cardioversion/defibrillation shocks, and a low voltage battery employed for powering the circuitry and delivering pacing pulses.

In one embodiment, housing 30 includes a first electrode 60 formed on a major surface of housing 30. In one embodiment, first electrode 60 is sized between about 100 mm2 and 1,000 mm2, for example, and is formed of a solid conductive sheet or a conductive mesh formed of a biocompatible electrode material, e.g., titanium, nickel alloys, stainless steel alloys, platinum, platinum iridium alloy, and mixtures thereof. When positioned, tissue adhesive may be employed to secure housing 30 at the desired subcutaneous site and prevent migration. Alternatively, the site is exposed through a minimally invasive surgical procedure and housing 30 is sutured at the site to prevent device migration. The resulting cosmetic appearance can be improved by forming the housing 30 to be as thin as possible, minimizing the bulk of header 32 and curving the major housing surfaces to conform well to the curvature of the thorax at the recommended posterior and anterior or other implantation sites.

In one embodiment, header 32 is configured for permanent connection to proximal end 36 of lead 34. In one embodiment, header 32 is configured for removable connection with proximal end 36 of lead 34.

Figure 2:
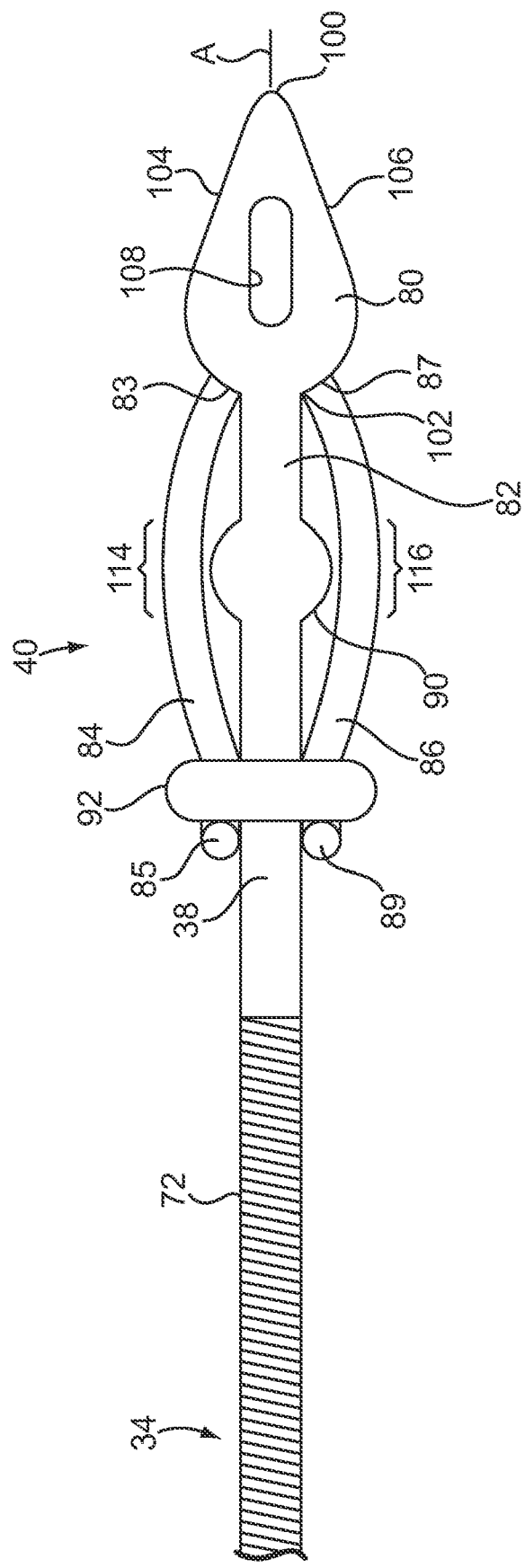
FIG. 2 is a top view of the lead and the lead tip of FIG. 1.

FIG. 2 is a top view of lead tip 40 attached to lead 34 and oriented along a central longitudinal axis A. In one embodiment, lead tip 40 includes a head 80, a body 82 extending between head 80 and lead 34, a first movable arm 84 including a first end 83 attached to head 80 and a second end 85 movable relative to head 80, and a second movable arm 86 including a first end 87 attached to head 80 and a second end 89 movable relative to head 80. In one embodiment, at least two laterally movable arms are provided. In one embodiment, multiple movable arms are provided that move radially away from body 82 laterally and in the plane of the printed image as illustrated.

In one embodiment, body 82 includes a waist 90 defined by a bulge extending radially from body 82. Second ends 85, 89 of movable arms 84, 86, respectively, are configured to slide along body 82 and engage with waist 90 in a manner that laterally extends arms 84, 86 for fixation into tissue of the patient. In one embodiment, an elastic ring 92 is provided to compress second ends 85, 87 into engagement with waist 90 to selectively retain movable arms 84, 86 in the deployed position.

In one embodiment, head 80 includes a leading end 100 opposite a trailing end 102, and first and second non-parallel sides 104, 106 that taper down and converge with leading end 100. Trailing end 102 couples with body 82 and lead 34. First and second non-parallel sides 104, 106 that taper to an apex formed by leading end 100 such that head 80 is arrow-shaped or triangular in longitudinal cross-section. At least the apex of head 80 is configured to part subcutaneous tissue without cutting through the skin or the thorax. In one embodiment, head 80 is formed to define an opening 108 between leading end 100 and trailing end 102, where opening 108 is configured for engagement with a tunneling tool that is employed to subcutaneously place lead 34.

In one embodiment, each arm 84, 86 includes a central portion 114, 116, respectively, that is configured to diverge laterally away from axis A when second ends 85, 89, respectively, are moved axially toward head 80. In this regard, central portions 114, 116 lie adjacent to body 82 when in a tunneling state and are configured to expand laterally away from central axis A into a deployed state in which central portions 114, 116 are offset away from body 82. In one embodiment, lead tip 40 has a cross-sectional lateral dimension of about 3.5 mm when in the tunneling state, and is deployed to have a cross-sectional lateral dimension of between about 10-25 mm when in the deployed, fixed state.

Suitable materials for fabrication of lead tip 40 include plastic or metal. In one embodiment, at least movable arms 84, 86 are formed of a flexible plastic such as silicone, silicone rubber, or polyurethane. In one embodiment, the entire lead tip 40 including head 80, body 82 and movable arms 84, 86 are integrally formed of a plastic. In another embodiment, movable arms 84, 86 are formed of a plastic and at least a portion of lead tip 40 (e.g., head 80 or body 82) is formed to include an electrically conductive material. In one embodiment, elastic ring 92 is formed of a silicone rubber that is configured to stretch to enable second ends 85, 89 to clear waist 90 as second ends 85, 89 axially traverse body 82.

Figure 3:
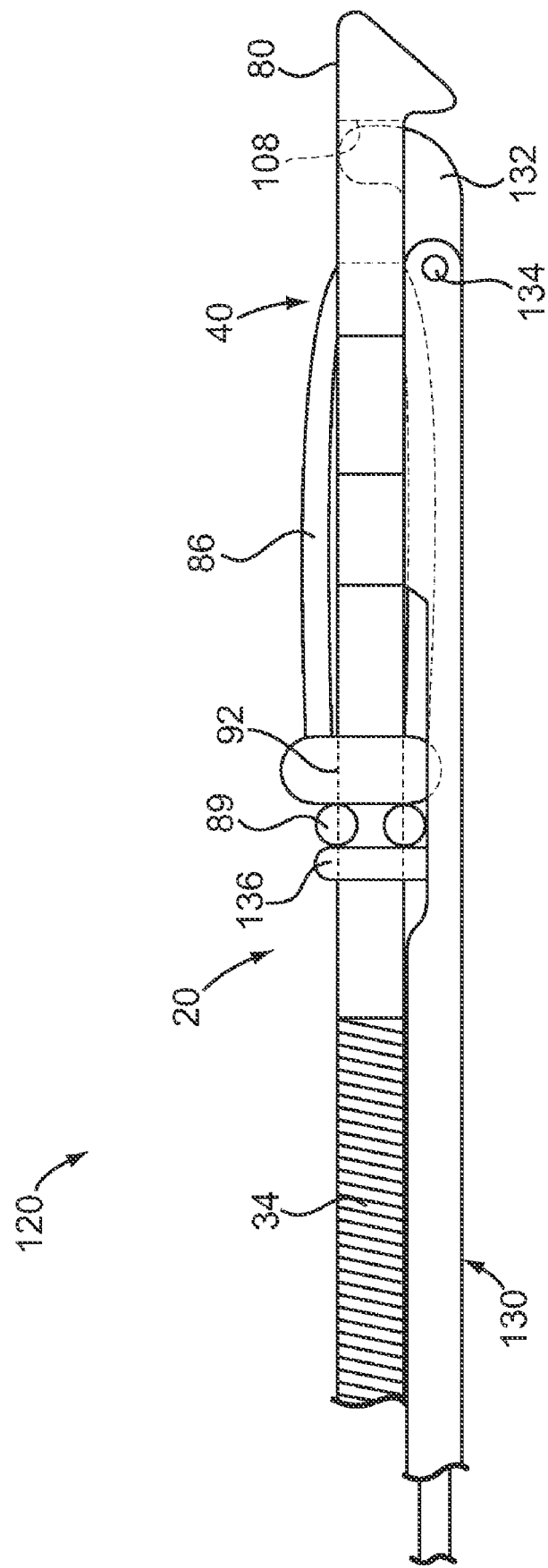
FIG. 3 is a side view of a subcutaneous implantable lead system including a tunneling tool engaged with the lead tip illustrated in FIG. 2 according to one embodiment.
Figure 4:
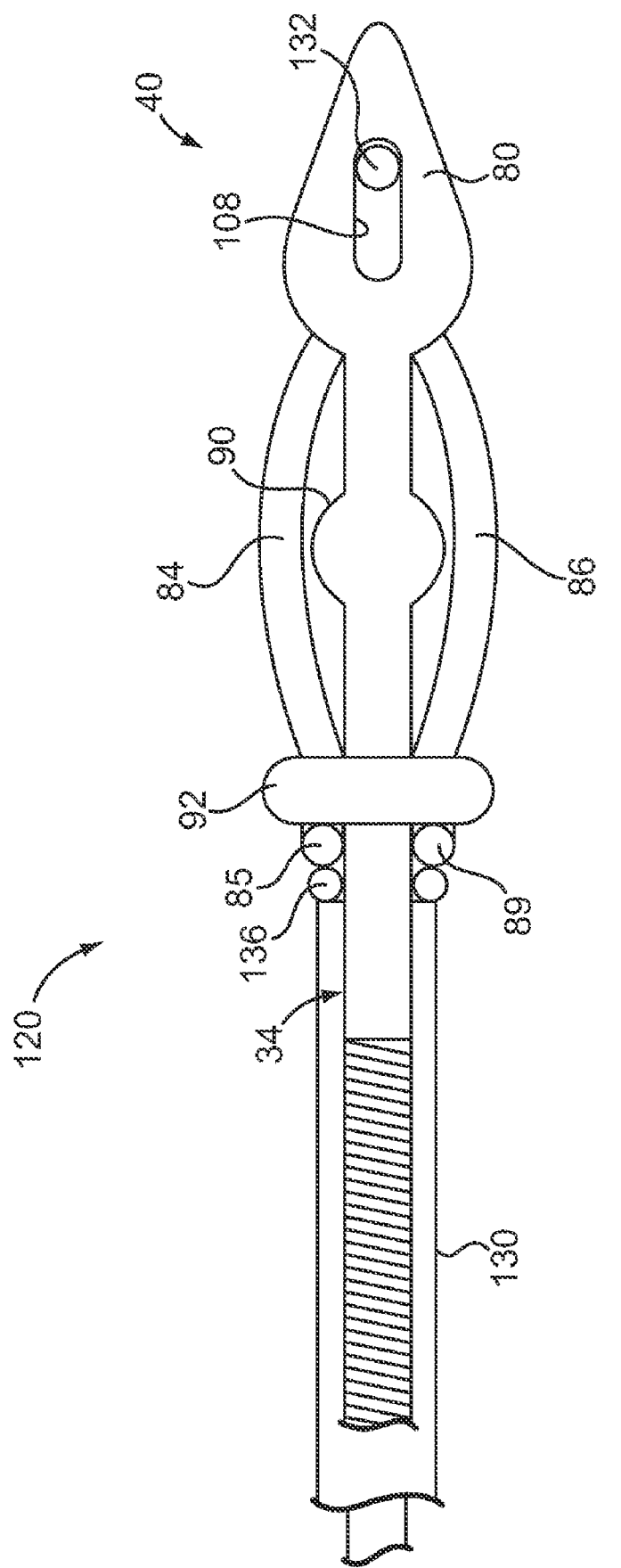
FIG. 4 is a top view of the lead system illustrated in FIG. 3 showing the lead tip in an implantation configuration where arms of the lead tip are relaxed alongside a body of the lead tip.

FIG. 3 is a side view and FIG. 4 is a top view of a subcutaneous implantable lead system 120 according to one embodiment. System 120 includes a tunneling tool 130 having a finger 132 that is configured to engage with opening 108 formed in head 80 of lead tip 40. In one embodiment, tunneling tool 130 includes a hinge 134 and a movable flange 136 that are configured to be activated by wires extending between hinge 134/flange 136 and a handle on a proximate end of tunneling tool 130.

Activating hinge 134 (from the proximal end of tunneling tool 130) moves finger 132 into engagement with opening 108 and out of engagement with opening 108. Finger 132 is engaged with opening 108 to couple tunneling tool 130 to lead tip 40 prior to subcutaneously advancing lead tip 40. After advancing lead 34, flange 136 is activated from the proximal end of tunneling tool 130 to push second ends 85, 89, toward head 80 and fix arms 84, 86 into tissue. Thereafter, finger 132 is removed from opening 108 to disengaged tunneling tool 130 from lead tip 40 after subcutaneously advancing and distally fixing lead tip 40 in place. In one embodiment, movable arms 84, 86 are co-planar and aligned alongside body 82, where the co-planar plane may be either a vertical or lateral plane. In one embodiment, movable arms 84, 86 are aligned alongside body 82 with movable arm 84 offset above, and not co-planar, with movable arm 86.

Figure 5:
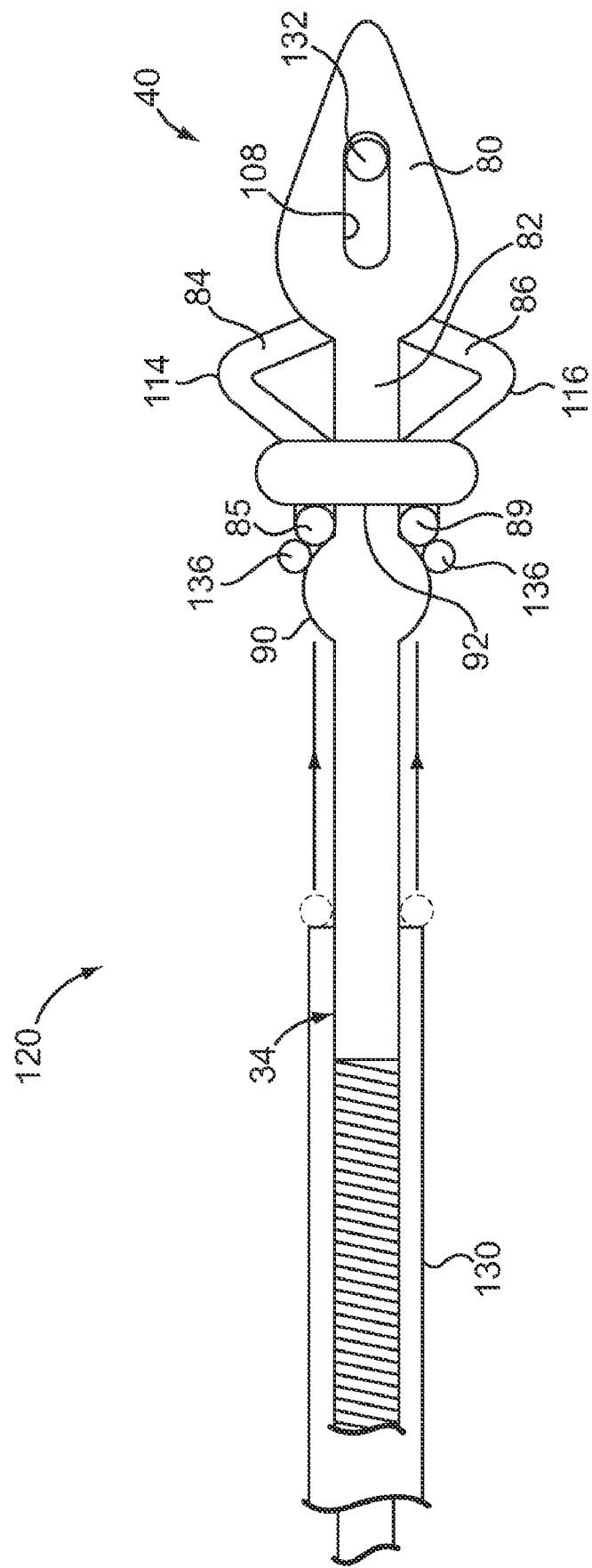
FIG. 5 is a top view of the lead system illustrated in FIG. 3 showing the arms deployed proximally via the tunneling tool to a distal fixation configuration according to one embodiment.

FIG. 5 is a top view of flange 136 advanced distally to slide second ends 85, 89 over waist 90 and laterally displace central portions 114, 116 of arms 84, 86 into their deployed positions. When deployed, central portions 114, 116 of movable arms 84, 86 extend from body 82 to fix and anchor lead tip 40 into tissue (i.e., fat tissue). Flexible ring 92 constricts ends 85, 89 into position on a distal side of waist 90. In this manner, lead tip 40 is tunneled into position with tunneling tool 130 and distally activated by manipulating a proximal end of tunneling tool 130 to expand arms 114, 116 and anchor lead tip 40 subcutaneously.

Figure 6:
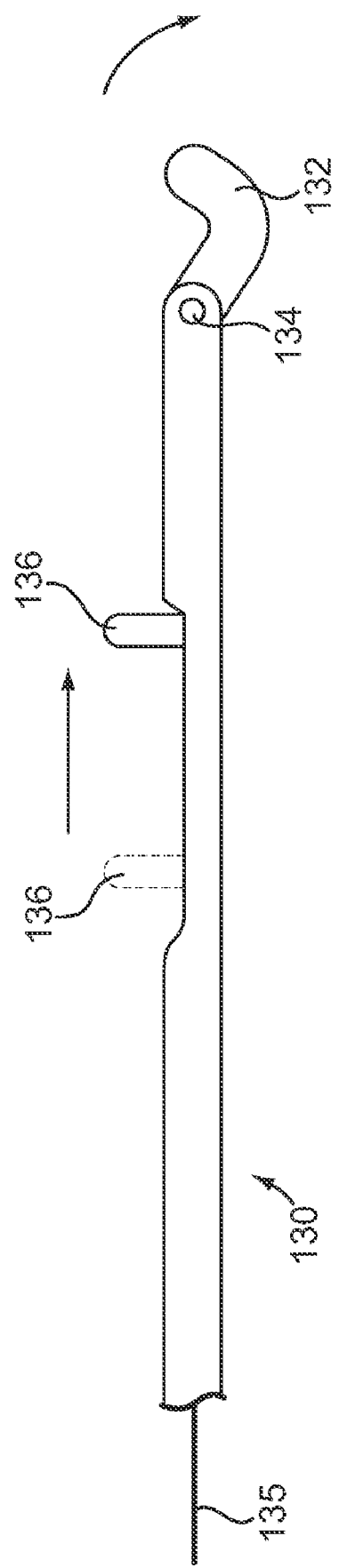
FIG. 6 is a side view of the tunneling tool disengaged from the lead tip according to one embodiment.

FIG. 6 is a side view of tunneling tool 130 having finger 132 rotated out of engagement with opening 108 (FIG. 5). A wire 135 is located coaxially within tunneling tool 130 and communicates with hinge 134. Activating wire 135 proximally (for example by pulling) rotates finger 132 downward to unlock tunneling tool from lead tip 40 (FIG. 5). In one embodiment, a wire similar to wire 135 is employed to displace flange 136 distally to deploy lead tip 40 (FIG. 5) into its expanded state. Other deployment mechanisms apart form wires, such as pneumatic activation, direct connection via rods, etc are also acceptable for proximally activating the distal deployment mechanisms.

Figure 7A:
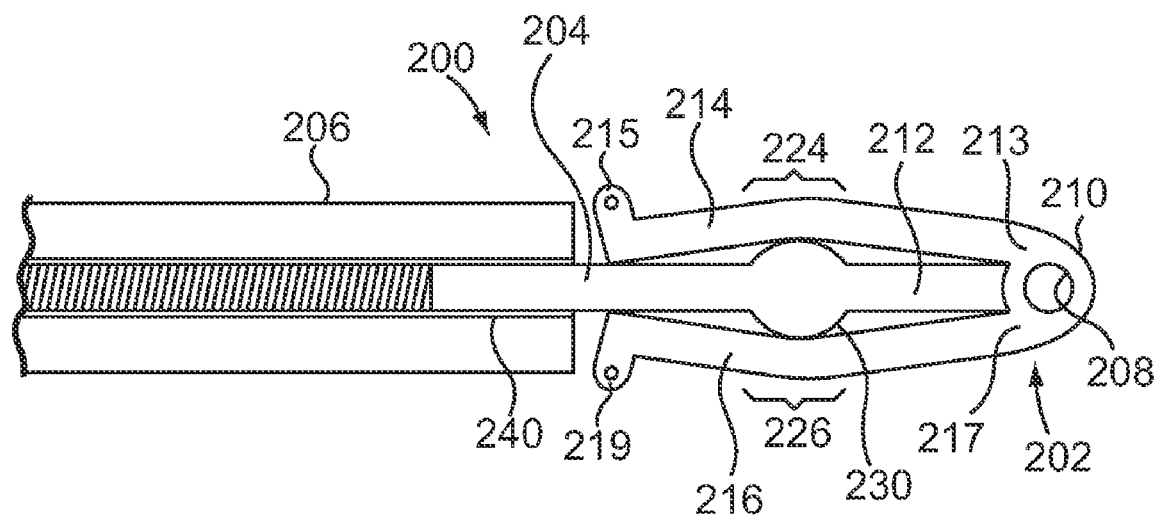
FIG. 7A is a top view of a subcutaneous implantable lead system including a lead tip and push tubing according to one embodiment.

FIG. 7A is a top view of another subcutaneous implantable system 200 according to one embodiment. System 200 includes a lead tip 202 coupled to a lead 204 and a tubular member 206 configured to activate and anchor lead tip 202 in subcutaneous tissue.

In one embodiment, lead tip 202 includes a head 210, a body 212 extending between head 210 and lead 204, a first arm 214 including a first end 213 attached to head 210 and a second end 215 that is movable relative to head 210, and a second arm 216 including a first end 217 attached to head 210 and a second end 219 that is movable relative to head 210. Similar to lead tip 40 described in FIG. 2 above, arms 214, 216 are configured to move axially along body 212 to move central portions 224, 226 laterally away from body 212. In one embodiment, body 212 includes a waist 230 extending radially away from body 212 to form a bulge that is configured to engage with second ends 215, 219. Although not shown for ease of illustration, in one embodiment an elastic ring is provided to compress second ends 215, 219 into engagement with waist 230 to selectively retain movable arms 214, 216 in the deployed position In one embodiment, head 210 is formed to define an opening 208 configured to receive finger 132 of tunneling tool 130 (FIG. 6). In one embodiment, head 210 is formed to be substantially circular in lateral cross-section to provide a blunt distal leading end that is configured to part subcutaneous tissue without cutting through the skin or the thorax. Other suitable shapes for head 210 are also acceptable, including arrow-shapes and wedge-shapes.

Figure 7B:
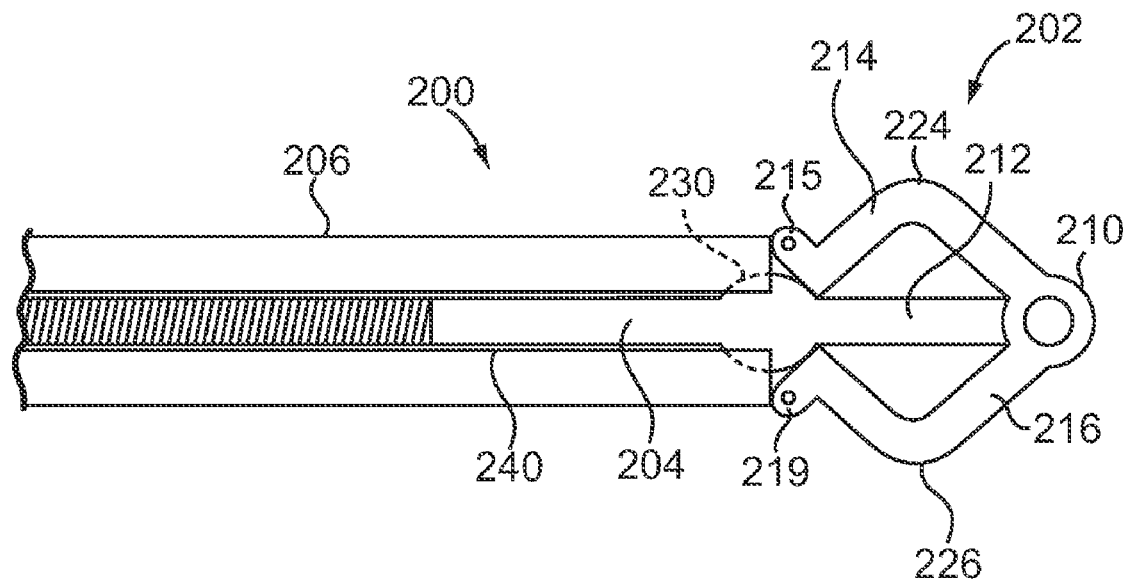
FIG. 7B is a top view of the lead system illustrated in FIG. 7A showing the push tubing employed to distally fix the lead tip in an expanded state according to one embodiment.

FIG. 7B is a top view of tubular member 206 moving second ends 215, 219 distally toward head 210. In one embodiment, lead tip 202 and lead 204 are delivered subcutaneously by a tunneling tool, such as tunneling tool 130 (FIG. 6). Lead 204 and tunneling tool 130 are disposed coaxially within tubular member 206 as lead 204 is delivered subcutaneously.

Tubular member 206 is manipulated from a proximal end exterior to the patient 22 (FIG. 1) to distally activate movable arms 214, 216 into engagement with subcutaneous tissue. In one embodiment, tubular member 206 pushes second ends 215, 219 over waist 230, second ends 215, 219 engage with a distal side of waist 230, and central portions 224, 226 of arms 214, 216 move laterally away from body 212. In this manner, arms 214, 216 are expanded to a deployed state characterized by an increased cross-sectional area of lead tip 202.

Figure 7C:
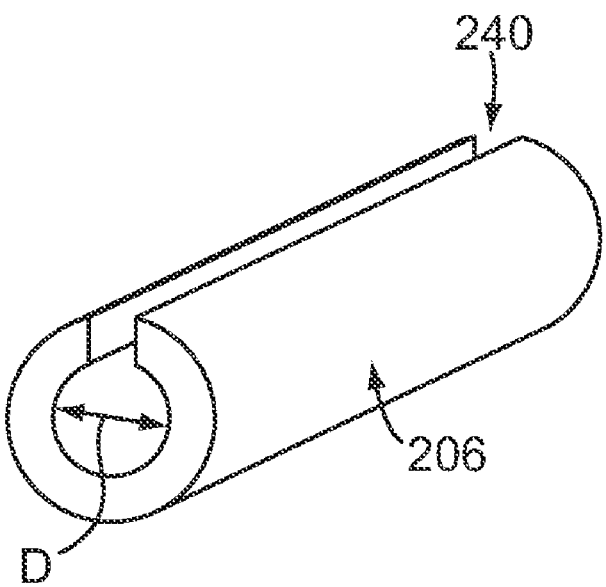
FIG. 7C is a perspective view of the push tubing illustrated in FIG. 7B.

FIG. 7C is a perspective view of tubular member 206 according to one embodiment. In one embodiment, tubular member 206 is formed to include a full-length axial channel 240 that is sized to enable tubular member 206 to disengage from tool 130 (FIG. 6) and lead 204 after placement of lead tip 202. In one embodiment, tubular member 206 includes an internal diameter D of approximately 1-3 mm that is sized to coaxially receive lead 204 and tunneling tool 130. In one deployment methodology, tunneling tool 130 is employed to subcutaneously implant lead tip 202, after which tunneling tool 130 is retrieved through tubular member 206. Thereafter, tubular member 206 is disengaged from lead 204 by sliding lead 204 through axial channel 240.

Figure 8:
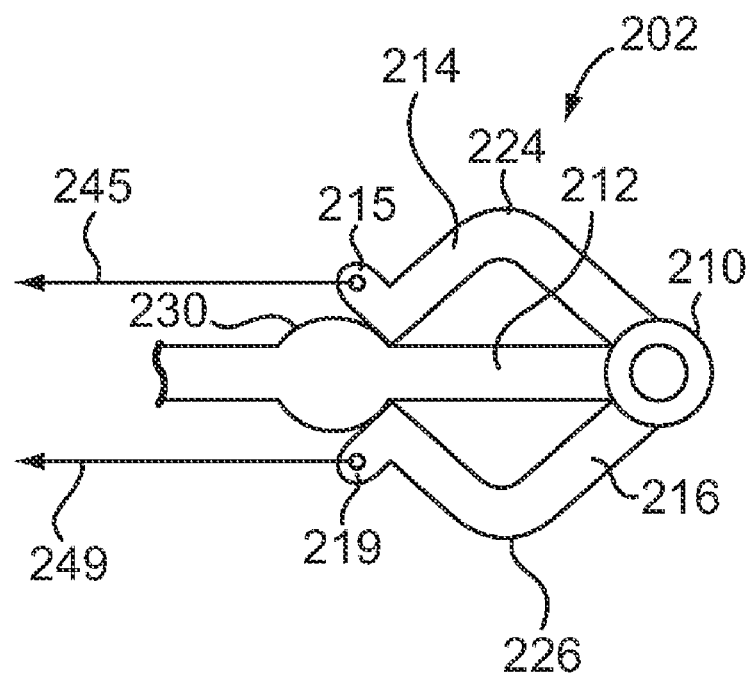
FIG. 8 is a top view of a lead tip for a subcutaneous implantable lead including pull wires configured to remove the lead tip according to one embodiment.

FIG. 8 is a top view of lead tip 202 including optional pull wires 245, 249 according to one embodiment. Lead tip 202 is illustrated in its deployed state having central portions 224, 226 laterally offset from body 212. Occasionally, it is desirable to remove lead 204 and lead tip 202 when managing the implantation site. Pull wires 245, 249 are provided and attached to lead tip 202 to enable collapsing movable arms 214, 216 along side body 212 prior to retrieving lead tip 202 from patient 22 (FIG. 1).

Pull wire 245 is coupled to second end 215 of movable arm 214, and pull wire 249 is coupled to second end 219 of movable arm 216. In one embodiment, pull wires 245, 249 are formed of an electrically non-conducting material and are implanted alongside lead 204 when lead tip 202 is subcutaneously implanted. To remove lead tip 202, pull wires 245, 249 are pulled proximally and second ends 215, 219, respectively, are displaced in a proximal direction over waist 230 such that arms 214, 216 collapses alongside body 212. In this manner, lead tip 202 is collapsed to have a cross-sectional dimension of about 3.5 mm to enable retrieval of lead tip 202 from the subcutaneous implantation site.

What is claimed is:

1. A subcutaneous implantable lead comprising:
a coil disposed along a portion of the lead; and
a lead tip coupled to a distal end of the lead and comprising at least one component that is movable relative to the distal end of the lead and configured to anchor the lead tip in subcutaneous tissue, wherein the lead tip comprises:
a head defining a leading end opposite a trailing end that is coupled to the distal end of the lead; and
at least one arm coupled to the head and comprising a first end attached to the head and a second end that is movable relative to the head, and wherein when the second end of the arm is moved axially toward the head a central portion of the arm moves laterally relative to the head to secure the implantable lead within subcutaneous tissue.

2. A subcutaneous implantable lead comprising:
a coil disposed along a portion of the lead; and
a lead tip coupled to a distal end of the lead and comprising at least one component that is movable relative to the distal end of the lead and configured to anchor the lead tip in subcutaneous tissue, wherein the lead tip comprises:
a head defining a leading end opposite a trailing end that is coupled to the distal end of the lead; and
at least one arm coupled to the head and comprising a first end attached to the head and a second end that is movable relative to the head, wherein the lead tip comprises a body coupled to the head, the body disposed along a central longitudinal axis of the head, the second end movable along the body relative to the head.

3. The subcutaneous implantable lead of claim 2, wherein the body comprises a waist defined by a bulge extending radially from the body, the second end of the arm configured to engage the waist and move an elbow portion of the arm laterally away from the body to anchor the lead tip in subcutaneous tissue.

4. The subcutaneous implantable lead of claim 3, comprising two arms coupled to the head, each arm comprising a first end attached to the head and a second end that is movable relative to the head and configured to engage the waist and move an elbow portion of the arm laterally away from the body.

5. The subcutaneous implantable lead of claim 3, further comprising:
an elastic ring coupled to the second ends of the lead tip, the ring configured to compress the second ends into engagement with the waist.

6. The subcutaneous implantable lead of claim 4, further comprising:
a wire coupled to each of the second ends of the arms, the wire configured to pull each second end of the arm toward a proximal end of the lead, disengage the second end of the arm from the waist, and move the elbow portion of the arm laterally toward the body for removal of the lead tip from the subcutaneous tissue.

7. A subcutaneous implantable lead comprising:
a coil disposed along a portion of the lead; and
a lead tip coupled to a distal end of the lead and comprising at least one component that is movable relative to the distal end of the lead and configured to anchor the lead tip in subcutaneous tissue, wherein the lead tip comprises:
a head defining a leading end opposite a trailing end that is coupled to the distal end of the lead; and
at least one arm coupled to the head and comprising a first end attached to the head and a second end that is movable relative to the head, wherein the head comprises an opening formed in the head located between the leading end and the trailing end, the opening configured for engagement with a tunneling tool.

8. A subcutaneous implantable lead comprising:
a coil disposed along a portion of the lead; and
a lead tip coupled to a distal end of the lead and comprising at least one component that is movable relative to the distal end of the lead and configured to anchor the lead tip in subcutaneous tissue, wherein the lead tip comprises:
a head defining a leading end opposite a trailing end that is coupled to the distal end of the lead; and
at least one arm coupled to the head and comprising a first end attached to the head and a second end that is movable relative to the head, wherein the head comprises first and second sides that extend from the trailing end and converge to an apex at the leading end to define a substantially triangular shape.

9. The subcutaneous implantable lead of claim 1, wherein the lead tip is formed from a polymer.

10. The subcutaneous implantable lead of claim 1, wherein the head and the at least one arm are integrally formed as a single piece.

11. The subcutaneous implantable lead of claim 1, wherein at least a portion of the lead tip is electrically conductive.

12. The subcutaneous implantable lead of claim 1, wherein the coil comprises a first electrode and a proximal end of the lead is coupled to an implantable cardiodefibrillator that comprises a second electrode.

13. A subcutaneous implantable lead system comprising:
a lead comprising a defibrillation electrode;
a lead tip coupled to a distal end of the lead and comprising at least one arm that is movable relative to a central axis of the lead tip;
a tunneling tool configured to removably couple with the lead tip and advance the lead tip subcutaneously; and
a tubular member movable axially along the tunneling tool to displace a portion of the arm laterally away from the central axis of the lead tip and anchor the lead tip in subcutaneous tissue, wherein the lead tip comprises a head defining a leading end opposite a trailing end that is coupled to the distal end of the lead, a recess formed in the head, and a distal end of the tunneling tool comprises a prong configured to engage with the recess formed in the head.

14. A subcutaneous implantable lead system comprising:
a lead comprising a defibrillation electrode;
a lead tip coupled to a distal end of the lead and comprising at least one arm that is movable relative to a central axis of the lead tip;
a tunneling tool configured to removably couple with the lead tip and advance the lead tip subcutaneously; and
a tubular member movable axially along the tunneling tool to displace a portion of the arm laterally away from the central axis of the lead tip and anchor the lead tip in subcutaneous tissue, wherein the tubular member comprises a channel opening formed in a wall of the tubular member between a proximal end and a distal end of the tubular member, the channel opening configured to enable removal of the tubular member from the subcutaneously implanted lead.

15. A method of implanting a lead in a patient, the lead attachable to an implantable cardiodefibrillator (ICD), the method comprising:
subcutaneously advancing a lead tip attached to a distal end of the lead through a surgical incision formed in the patient's skin with a tunneling tool that is removably attached to the lead tip; and
activating a movable portion of the lead tip from a proximal end of the lead to fix the distal end of the lead in subcutaneous tissue, wherein subcutaneously advancing a lead tip attached to a distal end of the lead comprises subcutaneously advancing a lead tip comprising a head defining a leading end aligned axially with a trailing end that is coupled to the distal end of the lead, and a movable arm coupled to the head that is movable radially away from the head, and wherein activating a movable portion of the lead tip comprises moving a proximal end of the movable arm axially toward the leading end of the head and displacing a central portion of the movable arm radially away from the head.

16. The method of claim 15, wherein activating a movable portion of the lead tip comprises coaxially moving a push tubing along the lead and engaging a proximal end of the push tubing with the proximal end of the movable arm.

17. The method of claim 16, wherein the lead tip comprises a body extending from the head, and moving a proximal end of the movable arm axially toward the leading end of the head comprises fixably engaging the proximal end of the movable arm over a waist formed in the body of the lead tip.

18. The method of claim 17, further comprising:
removing the lead and the lead tip from the patient by collapsing the movable arm alongside the body and retrieving the lead tip.

19. The method of claim 18, wherein collapsing the movable arm alongside the body comprises pulling a wire coupled to the proximal end of the movable arm and moving the proximal end of the movable arm axially toward the proximal end of the lead.

* * * * *